(12) United States Patent
Jin et al.

(10) Patent No.: US 11,857,192 B2
(45) Date of Patent: Jan. 2, 2024

(54) SELF-SERVICE ANASTOMOSIS CLAMP FOR DIGESTIVE TRACT AND DELIVERY SYSTEM THEREOF

(71) Applicant: MICRO-TECH (NANJING) CO., LTD., Jiangsu (CN)

(72) Inventors: Hongyan Jin, Jiangsu (CN); Zhenghua Shen, Jiangsu (CN); Weiqin Qiu, Jiangsu (CN); Zhou Yu, Jiangsu (CN); Zhi Tang, Jiangsu (CN)

(73) Assignee: MICRO-TECH (NANJING) CO., LTD., Jiangsu (CN)

( * ) Notice: Subject to any disclaimer, the term of this patent is extended or adjusted under 35 U.S.C. 154(b) by 51 days.

(21) Appl. No.: 17/096,257

(22) Filed: Nov. 12, 2020

(65) Prior Publication Data
US 2021/0059677 A1 Mar. 4, 2021

Related U.S. Application Data

(63) Continuation-in-part of application No. PCT/CN2018/111443, filed on Oct. 23, 2018.

(30) Foreign Application Priority Data

May 17, 2018 (CN) .......................... 201810474685.1

(51) Int. Cl.
*A61B 17/11* (2006.01)
*A61B 17/00* (2006.01)
(Continued)

(52) U.S. Cl.
CPC .... *A61B 17/1114* (2013.01); *A61B 17/00234* (2013.01); *A61B 17/122* (2013.01);
(Continued)

(58) Field of Classification Search
CPC ... A61B 17/11; A61B 17/1114; A61B 17/122; A61B 17/08; A61B 2017/00818;
(Continued)

(56) References Cited

U.S. PATENT DOCUMENTS 5,702,412 A * 12/1997 Popov .............. A61B 17/32053
606/159
5,817,113 A 10/1998 Gifford, III et al.
(Continued)

FOREIGN PATENT DOCUMENTS

CN 204581383 U 8/2015
CN 105997184 A 10/2016
(Continued)

OTHER PUBLICATIONS

International Search Report and Written Opinion for International PCT Application No. PCT/CN2018/111443, dated Feb. 20, 2019.

*Primary Examiner* — Timothy J Neal
*Assistant Examiner* — Mitchell Brian Hoag
(74) *Attorney, Agent, or Firm* — K&L Gates LLP

(57) ABSTRACT

An anastomosis clamp (1) and a delivery system thereof, where the anastomosis clamp (1) includes inner lancets (102, 602), round corners (103, 603), and outer rings (101, 601) that are sequentially connected; the delivery system may be used in cooperation with the anastomosis clamp (1); and the delivery system includes a distal end (2), a middle flexible sheath (3), and a handle (4).

15 Claims, 4 Drawing Sheets

(51) Int. Cl.
*A61B 17/122* (2006.01)
*A61B 17/15* (2006.01)

(52) U.S. Cl.
CPC .............. *A61B 17/11* (2013.01); *A61B 17/15* (2013.01); *A61B 2017/00269* (2013.01); *A61B 2017/00336* (2013.01); *A61B 2017/00862* (2013.01); *A61B 2017/00902* (2013.01); *A61B 2017/111* (2013.01); *A61B 2017/1107* (2013.01); *A61B 2017/1132* (2013.01)

(58) Field of Classification Search
CPC .......... A61B 14/10; A61B 2017/00296; A61B 147/083; A61B 17/115; A61B 2017/1107; A61B 2017/111; A61B 2017/1132; A61B 2017/1135; A61B 2017/1139; A61B 17/1146; A61B 2017/12004; A61B 17/12045; A61B 2017/12127
See application file for complete search history.

(56) References Cited

U.S. PATENT DOCUMENTS

| | | | | |
|---|---|---|---|---|
| 5,904,697 A * | 5/1999 | Gifford, III | ...... | A61B 17/12109 606/155 |
| 6,059,719 A * | 5/2000 | Yamamoto | ....... | A61B 17/00234 606/1 |
| 6,402,764 B1 * | 6/2002 | Hendricksen | .......... | A61F 2/064 606/149 |
| 6,565,581 B1 * | 5/2003 | Spence | .............. | A61B 17/1152 606/153 |
| 6,811,555 B1 * | 11/2004 | Willis | ................ | A61B 17/1152 606/151 |
| 9,289,214 B2 * | 3/2016 | Grönberg | ............ | A61B 17/1114 |
| 2002/0082614 A1 * | 6/2002 | Logan | .................... | A61B 17/11 606/139 |
| 2003/0144676 A1 * | 7/2003 | Koster, Jr. | .............. | A61B 17/11 606/155 |
| 2005/0023325 A1 * | 2/2005 | Gresham | ................ | A61B 17/115 227/176.1 |
| 2005/0055022 A1 * | 3/2005 | Schubert | ............ | A61B 18/1442 606/49 |
| 2005/0075655 A1 * | 4/2005 | Bumbalough | ..... | A61B 17/1285 606/153 |
| 2005/0149075 A1 * | 7/2005 | Borghi | .................... | A61B 17/11 606/153 |
| 2006/0155312 A1 * | 7/2006 | Levine | ............... | A61B 17/0401 606/153 |
| 2007/0167964 A1 | 7/2007 | Willis | | |
| 2007/0225762 A1 * | 9/2007 | LaBombard | ........ | A61B 17/0644 606/219 |
| 2011/0095069 A1 * | 4/2011 | Patel | .................. | A61B 17/1155 227/180.1 |
| 2013/0274771 A1 * | 10/2013 | Williams | ............. | A61B 17/072 606/153 |
| 2014/0217148 A1 * | 8/2014 | Penna | .............. | A61B 17/07292 227/140 |
| 2015/0094744 A1 * | 4/2015 | Aghayev | ................ | A61B 17/11 606/153 |
| 2017/0164950 A1 * | 6/2017 | Wright | .................. | A61B 17/128 |
| 2022/0304695 A1 * | 9/2022 | Miao | .................... | A61B 17/122 |

FOREIGN PATENT DOCUMENTS

| | | |
|---|---|---|
| CN | 107374685 A | 11/2017 |
| CN | 107374691 A | 11/2017 |
| CN | 108577917 A | 9/2018 |
| EP | 0957775 B1 | 4/2009 |
| WO | 2019218592 A1 | 11/2019 |

* cited by examiner

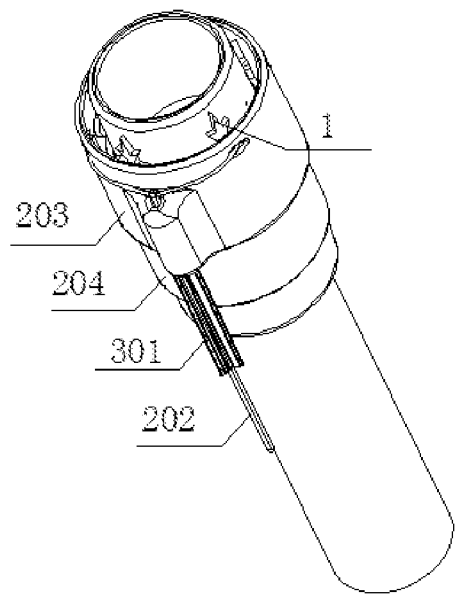
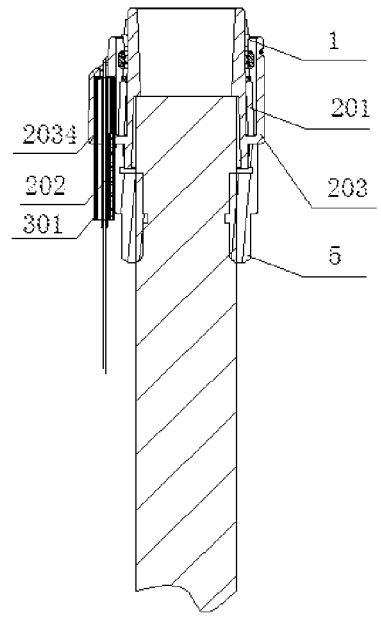
Fig. 7A    Fig. 7B
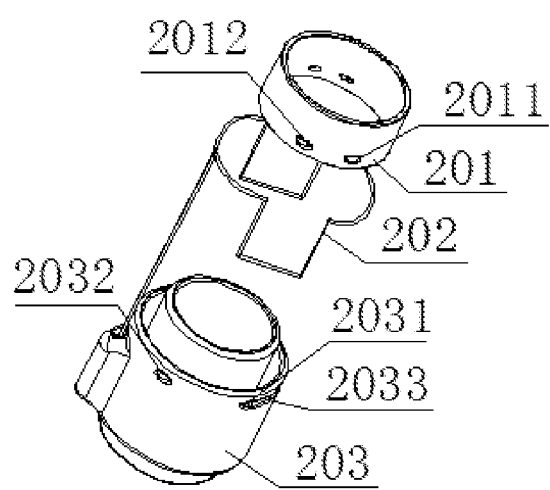
Fig. 8

SELF-SERVICE ANASTOMOSIS CLAMP FOR DIGESTIVE TRACT AND DELIVERY SYSTEM THEREOF

CROSS-REFERENCE TO RELATED APPLICATIONS

This application is a continuation-in-part of PCT Application Serial No. PCT/CN2018/111443, filed Oct. 23, 2018, entitled SELF-SERVICE ANASTOMOSIS CLAMP FOR DIGESTIVE TRACT AND DELIVERY SYSTEM THEREOF, and which claims priority to Chinese Provisional Application No. 201810474685.1, which was filed on May 17, 2018. The contents of each are incorporated by reference into this specification.

FIELD OF THE INVENTION

The present application relates to medical appliances, and in particular, to a self-service anastomosis clamp for digestive tract and a delivery system thereof. The present application further relates to specific structures and use methods of the anastomosis clamp and the delivery system.

BACKGROUND OF THE INVENTION

With development of the minimally invasive technology with an endoscope, recently, most clinical hemostasis and perforation closing after a minimally invasive surgery with an endoscope are clinically implemented in a hemostatic manner in which a hemostatic clamp is mainly used. The hemostatic clamp clamps a mucosa layer of a tissue by a mechanical squeezing principle to apply clamping, and the clamp, after being released, is left in the body. After a wound tissue completes self healing, tissues of clamped regions will gangrene and drop due to clamping force, and the clamp is excreted to the outside of the body together with the dropped tissue through a digestive tract. A remaining length of a hemostatic clamp for clamping is greater than 10 mm. Hemostatic clamps are clamped onto a mucosa layer in a way perpendicular to a wall of the digestive tract after being released. Thus, the hemostatic clamp is probably shifted or dropped due to peristalses of a digestive system, eating, external force to abdomen, or other reasons. Particularly, when a relatively large wound surface or perforation clinically occurs, it is difficult for a hemostatic clamp to realize an effective clamping effect due to small clamping force, a limited opening size, or other reasons.

Patent CN101453957, for improving a closure effect of a hemostatic clamp, describes a self-closing tissue fastener used for wound closure and surgeries, including a central ring and a tissue-piercing spine. By applying torsion energy, the fastener changes from a substantially planar structure into a substantially cylindrical structure. However, partial stress concentration may occur during a torsion process. As a result, the product may be fractured and damaged because stability becomes worse. Moreover, the tissue fastener has several protrusions at an outermost side, thus greatly stimulating the digestive tract. Thus, the tissue fastener may also scratch side walls of the digestive tract during a process of being excreted to the outside of the body. Further, when being used in cooperation with an endoscope, the delivery system can only be used after the endoscope and the guiding member are fixed first by using rubber rings or other connection accessory. The operation is complex and time consuming.

Therefore, a demanding requirement in the field is to provide an anastomosis clamp that may quickly repair damages to the digestive tract without scratching the digestive tract, and meanwhile may be easily operated.

Meanwhile, at present, an existing delivery system for deploying an anastomosis clamp in the market has a relatively long guiding member, and a plurality of outer lancets and/or protrusions are present on the outer side the guiding member. Therefore, when entering the body of a patient, the delivery system may bring damages to the patient.

SUMMARY OF THE INVENTION

An objective of the present application is to design a self-service anastomosis clamp for digestive tract and a delivery system thereof. Among which, in cooperation with the delivery system, the anastomosis clamp may quickly close acute bleeding, a fistula, fissure, and a perforation of a gastrointestinal tract of a digestive tract at one time. The anastomosis clamp may provide a large clamping force and would not easily lose its clamping force due to internal or external factors. For a relevant lesion, special requirements of first clamping and then resection (including full thickness resection) may also be met. The product has good stability during a process of deploying or clamping the anastomosis clamp, and may moderate fractures induced by partial stress concentration. Meanwhile, the digestive tract is merely slightly stimulated, and a side wall of the digestive tract will not be easily scratched.

According to a first aspect, the present application provides an anastomosis clamp, including: a plurality of outer rings, round corners, and inner lancets that are sequentially connected, with the whole connection structure being central symmetric; wherein the plurality of outer rings are spaced apart and are discontinuous, with adjacent discontinuous outer rings being connected via the round corners; wherein each round corner is provided with one inner lancet that is pointedly configured; wherein in a direction from the outer ring towards a center point of the symmetric connection structure, two round corners that are configured to curve in opposite directions are connected to form an S-like shape that connects the inner lancet to the outer ring; and wherein in the obtained connection structure, arc transitions are formed between the outer rings and the round corners.

In the anastomosis clamp according to the present application, the plurality of outer rings forms a discontinuous and approximately circular ring that does not contain any protruding sharp portions.

In the anastomosis clamp according to the present application, the plurality of outer rings may form a discontinuous polygon.

In the anastomosis clamp according to the present application, when the anastomosis clamp is assembled onto a delivery system, the inner lancet thereof is everted from a center of the discontinuous ring, so that the anastomosis clamp in the delivery system to be released is in a cylindrical configuration.

In the anastomosis clamp according to the present application, an outer diameter of the delivery system in cylindrical configuration is greater than or equal to an outer diameter of the anastomosis clamp that is not assembled.

The anastomosis clamp according to the present application is made of a hyperelastic material.

The present application further provides an anastomosis clamp delivery system for assembling and deploying the anastomosis clamp, wherein the anastomosis clamp delivery system may be used in cooperation with the anastomosis clamp.

The delivery system according to the present application includes a distal end, a middle flexible sheath, and a handle; wherein the distal end comprises a pulling cable, and a transparent cap wherein the pulling cable passes through the transparent cap and is connected to the handle via the middle flexible sheath; and wherein the anastomosis clamp may be assembled within the transparent cap, with the anastomosis clamp being pressed against the pulling cable, so that the anastomosis clamp to be released is in its cylindrical configuration.

In the delivery system according to the present application, the distal end may further comprise a thrust ring that is placed in the transparent cap; the pulling cable passes and connects the thrust ring and the transparent cap; the pulling cable that passes the thrust ring and the transparent cap is connected to the handle via the middle flexible sheath; wherein an axial length of the thrust ring is smaller than that of the transparent cap; the anastomosis clamp may be assembled within the transparent cap, with the discontinuous ring formed by the outer rings of the anastomosis clamp abutting against the thrust ring, so that the anastomosis clamp to be released is in its cylindrical configuration.

In the delivery system according to the present application, the pulling cable sequentially passes through the thrust ring and the transparent cap and connects the two, and forms an Ω-like shape between the thrust ring and the transparent cap.

In the delivery system according to the present application, the transparent cap is a double-layered structure having transparent cap holes and a connection hole.

In the delivery system according to the present application, the anastomosis clamp is sleeved on an inner layer of the transparent cap, the discontinuous ring formed by the outer rings of the anastomosis clamp abuts against the thrust ring, and a tip end of the inner lancet does not exceed the distal end portion of the transparent cap.

In the delivery system according to the present application, the distal end further comprises a soft connection cap; wherein one end of the soft connection cap is connected to the transparent cap, and the other end is configured to be connectable with an endoscope.

In the delivery system according to the present application, the soft connection cap is made of an elastic material.

In the delivery system according to the present application, the middle flexible sheath is disposed along an axial direction of the anastomosis clamp delivery system.

In the delivery system according to the present application, the pulling cable is so threaded to first make one end of the pulling cable pass through two holes at one side of the transparent cap, make the other end of the pulling cable pass through two other holes symmetrically arranged at the other side of the transparent cap, join the two ends of the pulling cable together, and then connect the joined pulling cable to the handle via the middle flexible sheath In the delivery system according to the present application, the pulling cable is so threaded to first align respective four holes on the transparent cap and the thrust ring; then make one end of the pulling cable sequentially thread into the holes of the transparent cap and the holes of the thrust ring, and then sequentially thread out of the holes of the transparent cap and the holes of the thrust ring; in a similar way, make the other end of the pulling cable pass through the four symmetrical holes of the transparent cap and the thrust ring; and join the two ends of the pulling cable together, and then connect the joined pulling cable to the handle via the middle flexible sheath.

In the delivery system according to the present application, after the anastomosis clamp is assembled, the pulling cable located between the transparent cap and the thrust ring is in an Ω-like shape.

In the delivery system according to the present application, an end portion of the endoscope is clamped in the delivery system.

According to a second aspect, the present application provides anastomosis clamp, including: a plurality of outer rings, round corners, and inner lancets; wherein an end of the outer ring is successively connected to two round corners that are curved in opposite directions as so form an S-like shape between the outer ring and the inner lancet; wherein the plurality of outer rings forms a discontinuous ring shape; wherein one end of the inner lancet is connected to two S-like structures, and is arranged between two adjacent outer rings, so that these two adjacent outer rings are axially-symmetric arranged with respect to the inner lancet, wherein the other end of the inner lancet has a pointed configuration.

In the anastomosis clamp according to the present application, the plurality of inner lancets are central-symmetrically arranged on the ring shaped structure formed by the outer rings.

In the anastomosis clamp according to the present application, the plurality of outer rings are separately arranged by the round corners, and the plurality of outer rings together form a dis-continuous circular ring structure or a discontinuous polygon structure.

In the anastomosis clamp according to the present application, the inner lancet comprises a plurality of sharp corners that are axial-symmetrically arranged at both sides with respect to the tip of the inner lancet, so as to aid a piercing and clamping of tissues that need to be clamped.

In the anastomosis clamp according to the present application, the plurality of outer rings, round corners, and inner lancets together form an integral structure made of a hyper-elastic material.

The present application further provides an anastomosis clamp delivery system for deploying the above anastomosis clamp, including a distal end, a middle flexible sheath, and a handle, wherein the distal end comprises a pulling cable and a transparent cap, and the pulling cable passes through the transparent cap and is connected to the handle via the middle flexible sheath; and wherein the anastomosis clamp is provided within the transparent cap, with the anastomosis clamp being pressed against the pulling cable, so that the anastomosis clamp to be released, being confined by the transparent cap, is in its cylindrical configuration.

In the delivery system according to the present application, the distal end further comprises a thrust ring; wherein the thrust ring is placed in the transparent cap; the pulling cable passes in a loop way and connects the thrust ring and the transparent cap; the pulling cable that passes the thrust ring and the transparent cap is connected to the handle via the middle flexible sheath; an axial length of the thrust ring is smaller than that of the transparent cap; and the discontinuous ring formed by the outer rings of the anastomosis clamp abuts against the thrust ring.

In the delivery system according to the present application, the pulling cable sequentially passes through the thrust ring and the transparent cap, and forms an Ω-like loop structure between the thrust ring and the transparent cap.

In the delivery system according to the present application, the transparent cap has a double-layered structure provided with a first transparent cap holes, a second transparent cap holes, and a connection hole.

In the delivery system according to the present application, one end of the pulling cable threads through two second transparent cap holes provided at one side of the transparent cap, the other end of the pulling cable threads through two first transparent cap holes provided at the respective other side of the transparent cap, and the two ends of the pulling cable are joined together, and are connected to the handle via the middle flexible sheath.

In the delivery system according to the present application, the anastomosis clamp is sleeved on an inner side of the transparent cap, such that the dis-continuous ring formed by the outer rings of the anastomosis clamp abuts against the thrust ring, and a tip end of the inner lancets of the anastomosis clamp does not exceed the distal end portion of the transparent cap.

In the delivery system according to the present application, the soft connection cap has a tube configuration made of an elastic material.

In the delivery system according to the present application, the endoscope may be snap-fitted within the soft connection cap.

BRIEF DESCRIPTION OF THE DRAWINGS

FIG. 7A is a sectional view of an anastomosis clamp delivery system shown in FIG. 6;

FIG. 7B is a sectional view of an anastomosis clamp delivery system shown in FIG. 6; and FIG. 8 is a schematic diagram showing threading of a pulling cable in an anastomosis clamp delivery system shown in FIG. 6.

REFERENCE NUMBERS

Figure 1:
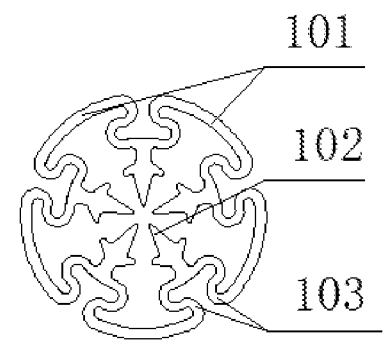
FIG. 1 is a schematic structural diagram of an anastomosis clamp.

1 Anastomosis Clamp
101, 601 Outer Rings
102, 602 Inner Lancets
103, 603 Round Corners
2 Distal end
201 Thrust Ring
202 Pulling cable
203 Transparent Cap
204 Soft Connection Cap
2031, 2032 Transparent Cap Holes
2033 Cable Trough
2034 Connection hole
2011, 2012 Thrust Ring Holes
3 Middle Flexible sheath
301 Flexible Outer Pipe
302 Internal Operation cable
4 Handle
401 Core Bar
402 Slider
5 Endoscope

DETAILED DESCRIPTION OF THE EMBODIMENTS

Technical solutions of the present application are described in detail below with reference to the accompanying drawings. It should be understood that the specific embodiments described herein are merely used to explain the present application, and are not used to limit the present application. The scope of this application is not limited by these embodiments, and is subjected to the scope of the applied patent. Moreover, to provide clearer descriptions and enable a person skilled in the art to understand the content of this application, all parts in the figures are not necessarily drawn according to relative sizes. The ratio of some sizes to other related scales may be highlighted to be exaggerated, and irrelevant or unimportant details are not completely drawn, for simplicity of the drawings.

An anastomosis clamp is provided according to an embodiment of the present application. The anastomosis clamp includes a plurality of outer rings 101, round corners 103, and inner lancets 102 that are sequentially connected, wherein all components are arranged in an annular central symmetric way and the whole structure is central symmetric. The plurality of outer rings 101 is spaced apart and are discontinuous. Adjacent discontinuous outer rings 101 are connected via four the round corners 103. The outer ring 101 is combined with and connected to the round corner 103 to form an end-to-end streamline shape that is concaved towards a center of the ring at the round corner 103. Each round corner 103 is provided with one inner lancet 102 that is pointedly configured. The pointed end of inner lancet 102 is directed towards a central symmetry point of the outer ring 101, for piercing a tissue when the anastomosis clamp clamps. Two round corners 103 that are curved in opposite directions are connected to form an S-like shape so as to connect the inner lancet 102 to the outer ring 101; in the obtained connection structure, arc transitions are formed between the outer rings 101 and the round corners 103. In this way, the entire connection structure does not have a point where stress is concentrated, thus having higher stability.

Regarding the anastomosis clamp according to the present application, the plurality of outer rings 101 forms a discontinuous and approximately circular ring that does not contain any protruding sharp portions. According to another embodiment, the plurality of outer rings 601 may also form a discontinuous polygon, with other structures and performances being basically the same or similar to those of the anastomosis clamp according to the embodiment of the circular outer ring 101. The anastomosis clamp does not have a sharp part at an outer side, and therefore rarely stimulates a gastrointestinal tract. Thus, after dropping within the gastrointestinal tract, the product is excreted more smoothly along the digestive tract without scratching a side wall of the digestive tract.

Regarding the anastomosis clamp of the present application, when the anastomosis clamp is assembled onto the delivery system, the inner lancet thereof is everted from a center of the discontinuous ring, so that the anastomosis clamp in the delivery system to be deployed is in a cylindrical configuration.

Regarding the anastomosis clamp of the present application, an outer diameter of the delivery system in its cylindrical configuration is greater than or equal to an outer diameter of the anastomosis clamp that is not assembled.

The anastomosis clamp of the present application is made of a hyperelastic material, such as a nickel-titanium alloy material.

The present application further provides an anastomosis clamp delivery system for assembling and deploying the anastomosis clamp, wherein the anastomosis clamp delivery system can be used in cooperation with the anastomosis clamp.

The anastomosis clamp delivery system of the present application includes a distal end 2, a middle flexible sheath 3, and a handle 4. The distal end 2 includes a pulling cable 202, a transparent cap 203, and a soft connection cap 204. One end of the soft connection cap 204 is connected to the transparent cap 203, and the other end is connected to an endoscope 5. The pulling cable 202 passes through the transparent cap 203 and is connected to the handle 4 via the middle flexible sheath 3. The anastomosis clamp 1 may be assembled within the transparent cap 203. The anastomosis clamp 1 is pressed against the pulling cable 202, so that the anastomosis clamp 1 to be released is in its cylindrical shape. At this time, in the anastomosis clamp 1, the outer ring 101 is in contact with the pulling cable 202. In other words, when assembling the anastomosis clamp 1, the outer ring 101 of the anastomosis clamp 1 is in direct contact with the pulling cable 202 in the transparent cap 203, so that the horizontal pulling cable 202 is deformed due to a force towards a proximal end. In this case, the anastomosis clamp 1 may alternatively be that the round corner 103 is in contact with the pulling cable 202 while the outer ring 101 is clamped between the pulling cable 202 and the transparent cap 203. Since the outer ring 101 is discontinuous, during assembling, several sections of the outer ring 101 are clamped into a gap between the pulling cable 202 and the transparent cap 203, and are suspended on the pulling cable 202. In this way, the pulling cable 202 is deformed due to a force that is transmitted from the round corner 103 to a proximal end.

It is to be noted that the endoscope 5 and the transparent cap 203 may be connected via the soft connection cap 204. As an alternative, one end of the transparent cap 203 may be configured to have a structure that matches with respective end of the endoscope 5, such that the end of the transparent cap 203 may be directly coupled to the endoscope 5 for connection.

Regarding the anastomosis clamp delivery system of the present application, the distal end 2 may further include a thrust ring 201. The thrust ring 201 is placed in the transparent cap 203. The pulling cable 202 passes and connects the thrust ring 201 and the transparent cap 203. The pulling cable 202 that passes the thrust ring 201 and the transparent cap 203 is connected to the handle 4 via the middle flexible sheath 3. An axial length of the thrust ring 201 is smaller than that of the transparent cap 203. The anastomosis clamp 1 may be assembled within the transparent cap 203. A discontinuous ring formed by the outer rings of the anastomosis clamp abuts against the thrust ring 201, so that the anastomosis clamp 1 to be released is in its cylindrical shape.

Regarding the anastomosis clamp delivery system of the present application, the pulling cable 202 sequentially passes through the thrust ring 201 and the transparent cap 203 and connects the two, and forms an Ω-like shape between the thrust ring 201 and the transparent cap 203.

Regarding the anastomosis clamp delivery system of the present application, the transparent cap 203 is a double-layered structure having transparent cap holes 2031, 2032 and a connection hole.

Regarding the delivery system of the present application, the anastomosis clamp is sleeved on an inner layer of the transparent cap 203, the discontinuous ring formed by the outer rings 101 of the anastomosis clamp abuts against the thrust ring 201, and a tip end of the inner lancet 102 does not exceed the distal end portion of the transparent cap 203.

Regarding the delivery system of the present application, the soft connection cap 204 is made of an elastic material, such as a soft rubber.

Regarding the delivery system of the present application, the middle flexible sheath 3 is disposed along an axial direction of the anastomosis clamp delivery system.

Regarding the delivery system of the present application, the pulling cable 202 is so threaded to first make one end of the pulling cable 202 pass through two holes at one side of the transparent cap 203, make the other end of the pulling cable 202 pass through two other holes symmetrically arranged at the other side of the transparent cap 203, join the two ends of the pulling cable 202 together, and then connect the joined pulling cable 202 to the handle 4 via the middle flexible sheath 3.

When the distal end 2 includes the thrust ring 201, the pulling cable is so threaded to: first align respective four holes on the transparent cap 203 and the thrust ring 201; then make one end of the pulling cable 202 sequentially thread into the holes of the transparent cap 203 and the holes of the thrust ring 201, and then sequentially thread out of the holes of the transparent cap 203 and the holes of the thrust ring 201; in a similar way, make the other end of the pulling cable 202 pass through the four symmetrical holes of the transparent cap 203 and the thrust ring 201; and join the two ends of the pulling cable 202 together, and then tighten and connect the joined pulling cable to the handle 4 via the middle flexible sheath 3. An inner operation cable 302 that is in the middle flexible sheath 3 and is directly connected to the pulling cable 202 may be replaced by an extension of the pulling cable 202.

Regarding the delivery system of the present application, after the anastomosis clamp 1 is assembled, the pulling cable 202 located between the transparent cap 203 and the thrust ring 201 is in an Ω-like shape. Therefore, when deploying the anastomosis clamp 1, a movement of the handle 4 towards a proximal end may drive the pulling cable 202 to move towards the proximal end, so as to drive the Ω-like shaped pulling cable 202 between the transparent cap 203 and the thrust ring 201 to be deformed. Further, because the pulling cable 202 is not flexible, after being applied with a force, a bottom portion of the Ω-like shaped pulling cable 202 tends to be lifted. In this way, the thrust ring 201 may push the delivery system towards a distal end, and the anastomosis clamp 1 is released from the delivery system. Compared with an anastomosis clamp delivery system in which a distal end 2 does not include a thrust ring 201, the thrust ring 201 according to the present invention may provide a more stable deploying process for the anastomosis clamp.

Regarding the delivery system of the present application, an end portion of the endoscope 5 is clamped in the delivery system. Specifically, the soft connection cap 204 of the distal end of the delivery system is made of an elastic material; the endoscope 5 is directly inserted into the soft connection cap 204, and may clamp an end portion of the endoscope 5 within the soft connection cap 204, such that the endoscope may be fixedly connected to the delivery system.

An anastomosis clamp 1 according to the embodiments of the present application is shown in FIG. 1 to FIG. 5.

Figure 2:
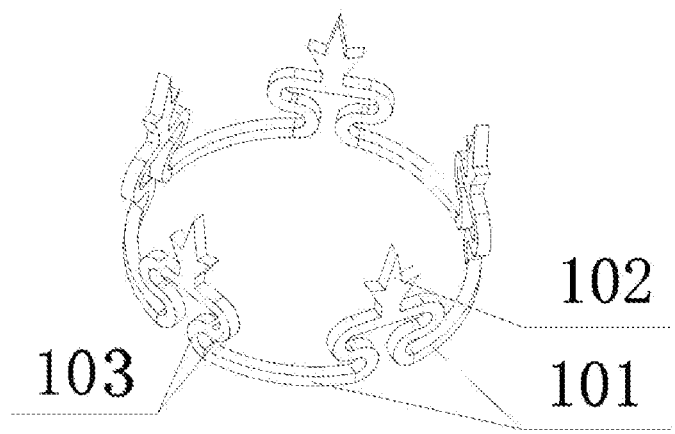
FIG. 2 is a diagram illustrating the anastomosis clamp shown in FIG. 1a in a to-be-released state.
Figure 3:
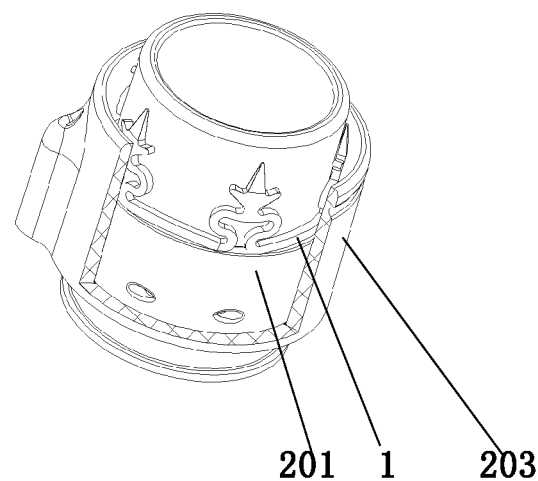
FIG. 3 is a diagram illustrating the anastomosis clamp shown in FIG. 1a that is arranged in a delivery system and is in a to-be-released state.

In a non-limiting embodiment of the present application, the anastomosis clamp includes outer rings 101, inner lancets 102, and round corners 103. FIG. 1 shows a schematic structural diagram of an anastomosis clamp that is constructed and operated according to an embodiment of the present application. FIG. 2 is a schematic structural diagram of a to-be-released anastomosis clamp shown in FIG. 1. FIG. 3 is a schematic structural diagram of a to-be-released circular anastomosis clamp in a delivery system shown in FIG. 1. The inner lancet 102, the round corner 103, and the outer ring 101 are sequentially connected, wherein all components are arranged in a central symmetric way.

The round corner 103 is in an arc configuration that is roughly semi-circular. Several outer rings 101 form a discontinuous ring with notches at an outermost side of the anastomosis clamp. Adjacent discontinuous outer rings 101 are connected via four round corners 103. The outer ring 101 is combined with and connected to the round corner 103 to form an end-to-end streamline shape that is concaved towards a center of the ring at the round corner 103. The entire connection structure does not have a point where stress is concentrated.

One end of the inner lancet 102 is connected to the round corner 103. The inner lancets 102 are central-symmetrically designed in a direction from the outer ring 101 towards the central symmetry point. The other end of the inner lancet 102 is sharp and is configured to pierce a tissue when the anastomosis clamp clamps. Several sharp corners may further be symmetrically distributed on the inner lancet 102, to assist piercing and clamping a tissue to be closed.

Adjacent discontinuous outer rings 101 are connected via four the round corners 103. According to a preferable embodiment, between the outer ring 101 and the inner lancet 102 and in a direction along which the outer ring 101 faces towards a center of the discontinuous ring, two arc-shaped round corners 103 in opposite directions are connected to form an S-like shape that connects the inner lancet 102 and the outer ring 101. In the obtained structure, arc transitions are formed between the outer ring 101 and the round corner 103.

The anastomosis clamp of the present application may not only prevent stress from being partially concentrated when its configuration is changed, but also further enables the anastomosis clamp to have higher stability when its configuration is changed. In other words, compared with a design in which the inner lancet 102 and the outer ring 101 are connected via a straight line or via another connection manner, the anastomosis clamp of the present application has greater clamping force, and requires greater force when its configuration is changed. The constitutional structure formed by S-like shaped round corners 103 are axis symmetrically distributed in the direction along which the outer ring 101 points towards the center of the discontinuous ring. Due to such a structure, a region between the inner lancet 102 and the outer ring 101 may be easily deformed elastically, so as to facilitate an arrangement of the anastomosis clamp in the delivery system. In other words, the anastomosis clamp may easily abuts against the thrust ring 201, such that the anastomosis clamp in its to-be-released state has a cylindrical configuration. Meanwhile, after being released, the constitutional structure formed by S-like shaped round corners 103 may resume its original ring configuration promptly to hitch around tissues.

When the anastomosis clamp of the present application is in a stationary state, as shown in FIG. 1, each outer ring 101 is in an arc curved shape, such that all outer rings 101 together form a discontinuous ring structure. This discontinuous ring structure does not have protruding sharp regions on it, thus rarely stimulates a gastrointestinal tract. Further, an anastomosis clamp with such a ring structure may easily drop off within the body, is excreted more smoothly along the digestive tract without scratching a side wall of the digestive tract.

Moreover, compared with a prior art anastomosis clamp in which the outer ring 101 bends inwards, an outer diameter of the anastomosis clamp of the present application in its ring state, provided that the same tissue volume is achieved, will be 20-30% smaller. Therefore, a feeling of foreign object to a patient may be effectively relieved and damages to a surrounding healthy tissue when the anastomosis clamp clamps a tissue may be reduced.

As shown in FIG. 2 and FIG. 3, when the anastomosis clamp of the present application is assembled to the delivery system and is in a to-be-released state, the inner lancet 102 is everted from the center of the discontinuous ring, so that a plane where the inner lancet 102 is located is substantially perpendicular to a plane where the discontinuous ring is located, such that the anastomosis clamp as a whole has a cylindrical configuration. During this everted process of the inner lancet 102, the round corners 103 are subjected to a torsional force, such that their arc-structure are deformed, causing the S-like shape formed by multiple round corners 103 to deploy. By this, a distance between adjacent outer rings 101 tends to be increased, such that an outer diameter of the discontinuous ring formed by the plurality of outer rings 101 of the anastomosis clamp may be greater than or equal to an outer diameter of the discontinuous ring when the anastomosis clamp is not assembled to the delivery system.

Figure 4:
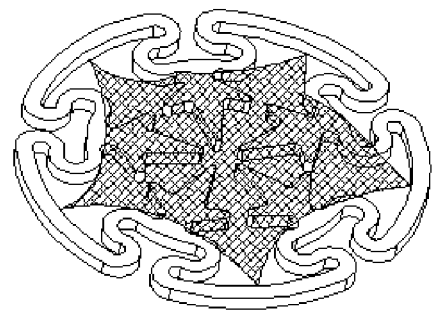
FIG. 4 is a schematic diagram of a released anastomosis clamp.

The outer ring 101 of the anastomosis clamp of the present application is in a straight-line shape or in an arc shape that bends outwards, thus may contain a larger area that can be used for clamping tissues. Therefore, if tissue volumes to be clamped are the same, an outer diameter of the anastomosis clamp of the present application is smaller than that of a prior art product. FIG. 4 shows a schematic diagram of the anastomosis clamp that is released to clamp tissues. The anastomosis clamp of the present application, when being assembled onto the delivery system, is in a cylindrical configuration. Due to a relatively small outer diameter, an axial length of the cylindrical configuration is relatively short. Thus, a delivery system required may have a shorter distal end, thus being easier to pass through a natural orifice of a human body. Moreover, the anastomosis clamp is substantially planar in its un-deformed configuration, facilitating a mounting on the delivery system.

The anastomosis clamp may be made of a hyperelastic material, such as a Ni—Ti alloy. A hyperelastic material may have excellent elastic deformation capacity, such that the anastomosis clamp may be adaptively deform from its to-be-released cylindrical configuration to the released planar configuration. At the same time, a hyperelastic material may also have good toughness, such that the inner lancet 102 may penetrate into tissues for clamping the tissues.

The whole structure formed by the inner lancet 102, the outer ring 101, and the round corner 103 has a smooth streamline profile. Such a structure does not have a portion where stress is concentrated. Therefore, the anastomosis clamp of the present application may have a higher reliability and stability, may effectively reduce probabilities of being damaged when the anastomosis clamp is in transferred into a to-be-released state due to external force, so that a tissue-clamping function thereof may be realized more stably, thus mitigating secondary injuries brought to the patient due to damage of the anastomosis clamp.

FIG. 4 is a schematic diagram of a released anastomosis clamp according to the present application. After the anastomosis clamp is released by using the delivery system, clamping force may be produced between the tips of the inner lancets 102, to well confine a pathological tissue within the outer ring 101. To improve penetrating force of the inner lancet 102 and better protect lining tissues of the human body, the tip of the inner lancet 102 needs to be ground. It is to be noted that the quantity and shape of the inner lancet 102 herein are not limited to those shown in the figures.

Figure 5:
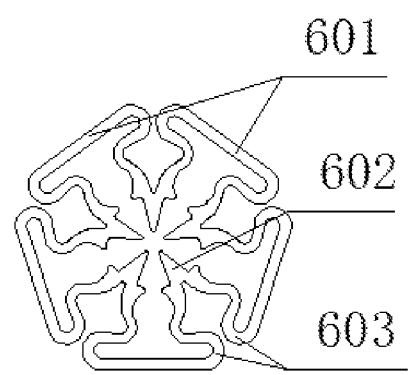
FIG. 5 is a schematic structural diagram of an anastomosis clamp according to another embodiment.

In a non-limiting embodiment of the present application, an anastomosis clamp 1 includes outer rings 601, inner lancets 602, and round corners 603. FIG. 5 shows a schematic structural diagram of an anastomosis clamp that is constructed and operated according to another embodiment of the present application. The outer rings 601 may alternatively be in a polygon structure, i.e., be a single outer ring 601 that does not have a curved arc region. However, because ends of the outer ring 601 is connected to the round corner 603, there is no protruding sharp portions, therefore, stimulation caused by the anastomosis clamp to the digestive tract may be reduced. Regarding the anastomosis clamp 1 according to this embodiment, except that the outer rings 601 together form a polygon structure, other structures and performances are basically the same or similar to those of the anastomosis clamp according to the embodiments of the outer ring 101.

It is to be noted that the anastomosis clamp of the present application may cooperate with any matching anastomosis clamp delivery system so as to be assembled and released.

Figure 6:
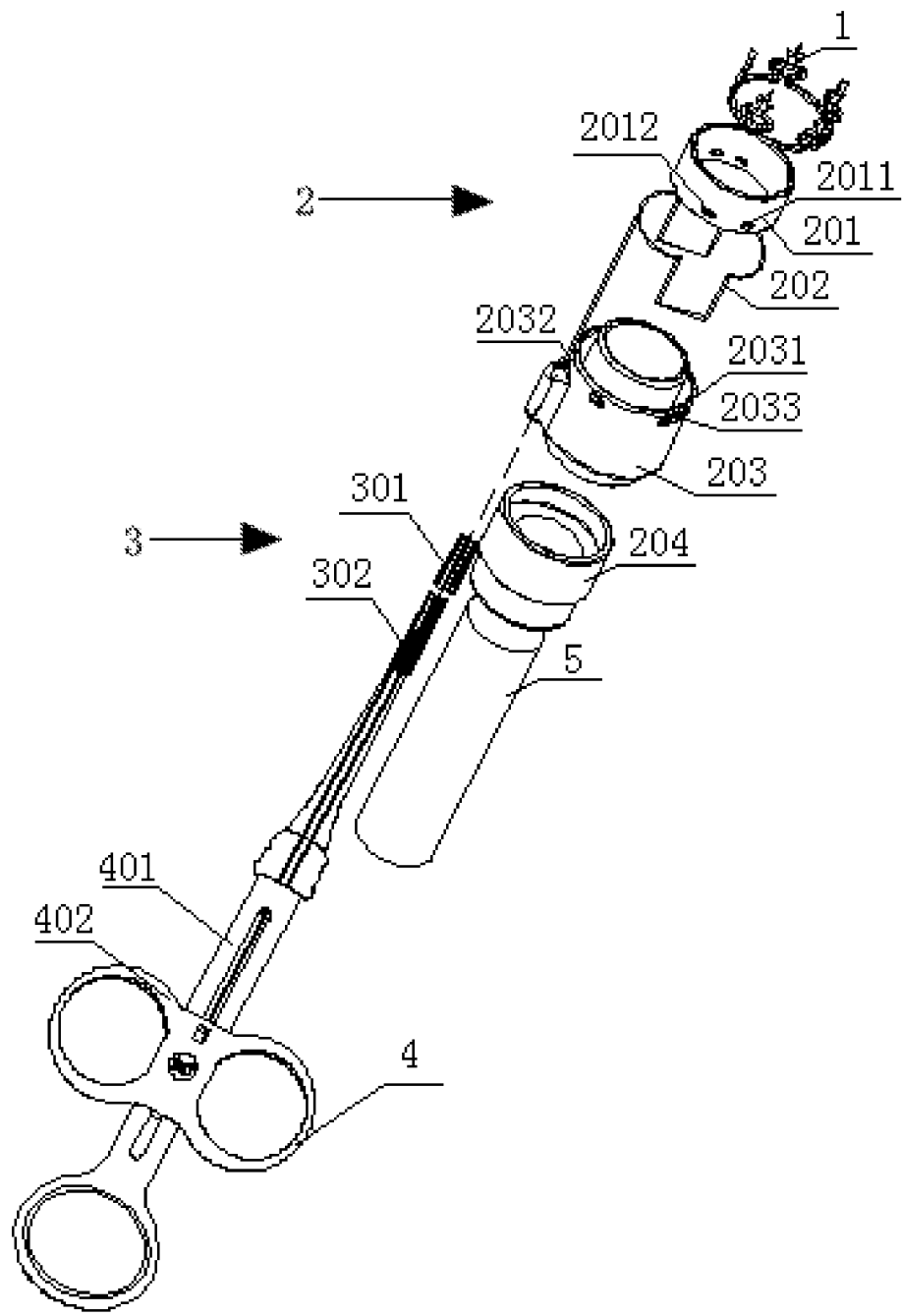
FIG. 6 is an exploded view of an anastomosis clamp delivery system that is suitable for an anastomosis clamp according to the present application.

In a non-limiting embodiment of the present application, as shown in FIG. 6 to FIG. 8, a delivery system suitable for the anastomosis clamp of the present application includes a distal end 2, a middle flexible sheath 3, and a handle 4. The distal end 2 includes a thrust ring 201, a pulling cable 202, a transparent cap 203, and a soft connection cap 204. The middle flexible sheath 3 includes a flexible outer pipe 301 and an intermediate operation cable 302. The handle 4 includes a core bar 401 and a slider 402. Among which, the thrust ring 201 is provided with thrust ring holes 2011 and 2012. The transparent cap 203 is provided with transparent cap holes 2031 and 2032, a cable trough 2033, and a connection hole 2034. The intermediate operation cable 302 may be replaced by an extension of the pulling cable 202.

FIG. 6 shows an exploded view of the delivery system. An end close to the handle 4 is referred to as a proximal end, and an end far away from the handle 4 is referred to as a distal end. The transparent cap 203 is a double-layered structure having the transparent cap holes 2031 and 2032, the cable trough 2033, and the connection hole 2034. The thrust ring 201 is a single-layered structure having the thrust ring holes 2011 and 2012. The thrust ring 201 is placed within a middle interbed of the double-layered transparent cap 203. The pulling cable 202 passes and connects the thrust ring 201 and the transparent cap 203. An axial length of the thrust ring 201 is smaller than that of the transparent cap 203.

When the anastomosis clamp 1 is assembled to the delivery system, the inner lancet of the anastomosis clamp 1 is everted from the center of the discontinuous ring, so that the to-be-released anastomosis clamp 1 in the delivery system is in a cylindrical configuration. The anastomosis clamp 1 in a cylindrical configuration is sleeved onto the inner layer of the transparent cap 203 having the double-layered structure. The outer ring 101 of the anastomosis clamp 1 abuts against the thrust ring 201. A tip end of the inner lancet does not exceed an end portion of the transparent cap 203.

One end of the soft connection cap 204 is sleeved onto the transparent cap 203, and the other end is connected to an endoscope 5. The soft connection cap 204 is connected to the endoscope 5 via snap-fitting. Because the soft connection cap 204 is made of an elastic material, such as soft PVC, silica gel, or a soft rubber, directly inserting the endoscope 5 into the soft connection cap 204 may clamp an end portion of the endoscope 5 within the soft connection cap 204, so as to be fixedly connect the endoscope 5 to the delivery system. Therefore, the delivery system of the present application and the endoscope may be easily connected, requiring less operation time.

The middle flexible sheath 3 is disposed along an axial direction of the delivery system. A distal end of the intermediate operation cable 302 passes through the connection hole 2034 and is connected to the pulling cable 202, and the proximal end thereof is connected to the handle 4. The distal end 2 of the delivery system is relatively short. Therefore, the delivery system of the present application has relatively less damages to a side wall of a gastrointestinal tract when passing through the bent gastrointestinal tract. Moreover, because there is no lancet or protrusion along the outer side the entire delivery system, damages to a tissue of the human body may be further reduced.

FIG. 7A and FIG. 7B respectively are an assembly diagram and a sectional view of a distal end and a part of a middle flexible sheath 3 of a delivery system of an anastomosis clamp 1 shown in FIG. 6. FIG. 8 is a threading schematic diagram of a pulling cable in an anastomosis clamp delivery system shown in FIG. 6. A specific threading manner of the pulling cable is: first aligning respective four holes on the transparent cap 203 and the thrust ring 201; subsequently, enabling one end of the pulling cable 202 to first simultaneously thread into the transparent cap hole 2031 and the thrust ring hole 2011, and then sequentially thread out from the thrust ring hole 2012 and the transparent cap hole 2032; enabling, in a same manner, the other end of the pulling cable 202 to sequentially pass through the four symmetrical holes of the transparent cap 203 and the thrust ring 201; and finally, enabling two ends of the pulling cable to pass into the connection hole 2034 shown in FIG. 7B after the two ends of the pulling cable are aligned and joined together, wherein the pulling cable 202 located between the transparent cap 203 and the thrust ring 201 is in an Ω-like shape, as shown in FIG. 8, and a body of the pulling cable is rightly embedded into the cable trough 2033 after the pulling cable 202 is tightened up.

When the anastomosis clamp is released, the handle 4 is moved towards the proximal end to drive the middle flexible sheath 3 that is connected to the handle 4 to move towards the proximal end. Further, because the intermediate operation cable 302 is connected to the pulling cable 202, the movement of the middle flexible sheath 3 towards the proximal end further drives the pulling cable 202 that passes through the connection hole 2034 to move towards the proximal end, so as to drive the pulling cable 202 that passes through the transparent cap 203 and the thrust ring 201 to be deformed. Because the material of the pulling cable 202 is not elastic, the Ω-like shaped pulling cable 202 that is located between the transparent cap 203 and the thrust ring 201 is deformed after being applied with force. Specifically, both sides of the Ω-like shaped pulling cable 202 are subjected to pulling force towards the outside, so that the Ω-like shaped pulling cable 202 tends to be straightened. In this way, the thrust ring 201 may push the delivery system towards a distal end, and the anastomosis clamp is released from the delivery system. Therefore, when the deploying action takes place, force acting on the anastomosis clamp 1 comes from two sections of the pulling cable. Meanwhile, since the thrust ring 201 and the pulling cable 202 are symmetrically designed, the thrust ring 201 may move toward the distal end smoothly. Furthermore, the transparent cap 203, as an inner structure, may be fitted as a guiding member to complete the action of deploying the anastomosis clamp 1.

According to an embodiment, the pulling cable 202 may be made of any material that is suitable for a human body. The material is not limited to a non-metallic material or a metal material; for example, the pulling cable 202 may be a stainless steel wire, a nickel-titanium wire, a PTFE wire, or the like.

During use of the delivery system, a preoperative assessment is made routinely, to determine a condition and a position of a lesion of the patient. The delivery system to which the anastomosis clamp 1 is mounted in advance is assembled with the endoscope 5 and is sent to the position with the lesion. An angle of the endoscope 5 is adjusted. When it is necessary, a wound surface is grasped by an assisting instrument or is sucked via negative pressure into the transparent cap 203 that is at the distal end. Afterwards, the handle 4 is moved towards the proximal end to drive the middle flexible sheath 3 that is connected to the handle 4 to move towards the proximal end. Meanwhile, the intermediate operation cable 302 drives the pulling cable 202 that passes through the connection hole 2034 to move towards the proximal end, so as to drive the Ω-like shaped pulling cable 202 that passes through the transparent cap 203 and the thrust ring 201 to be deformed, thus the thrust ring 201 may push the delivery system towards a distal end, and the anastomosis clamp 1 is released from the delivery system.

Since the anastomosis clamp 1 is made of a hyperelastic material, a certain amount of potential energy will be stored in the anastomosis clamp 1 that is assembled on a delivery system and takes a cylindrical configuration in a to-be-released state. After the anastomosis clamp 1 is pushed off from the delivery system, according to the minimum energy principle, since the external force that places restriction on the clamp is removed, the elastic potential energy will be converted into kinetic energy, so that the anastomosis clamp 1 may quickly clamp a root portion of the wound surface to realize the clamping function. At this time, the anastomosis clamp 1 will remain planar and stationary when there is no other external force, until a wound tissue completes self healing. Tissues in the clamped region will gangrene and drop due to clamping force, and the anastomosis clamp 1 is excreted to the outside of the body together with the dropped tissues through a digestive tract.

It can be seen that no matter the anastomosis clamp 1 is planar and stationary or is in a to-be-released state, the outer ring is nearly in an arc shape, thus avoiding unnecessary damages to the human body during use.

According to another embodiment of the present application, an anastomosis clamp is provided that includes a plurality of outer rings 101, round corners 103, and inner lancets 102. Among which, an end of an outer ring are successively connected to two round corners 103 that are curved in opposite directions and are connected to form an S-like shape so as to connect one inner lancet 102 to the outer ring 101. The plurality of outer rings 101 forms a discontinuous ring shape. One end of an inner lancet 102 is connected to two S-like structures formed by round corners 103, and is located between two adjacent outer rings 101, so that these two adjacent outer rings 101 are axially-symmetric provided with respect to the inner lancet 102. The other end of the inner lancet 102 has a pointed configuration.

For example, the anastomosis clamp may include five outer rings 101, with a round corner 103 being provided between any two neighboring outer rings 101. One end of the round corner 103 is connected to one respective outer ring 101 to form an arc transition at the correspond end of the outer ring 101, and the other end of the round corner 103 is connected to a further round corner 103 that is curved in an opposite direction for forming the S-like structure. Similarly, the other outer ring 101 is connected at one of its two ends with a further S-like structure formed by the other two round corner 103. The two S-like structures connected to these two neighboring outer rings 101 are both joined to the same inner lancet 102, such that the inner lancet 102 is formed between two neighboring outer rings 101.

It may be seen that by the above connection design that consists of outer rings 101, round corner 103, and inner lancet 102, the two symmetrically arranged S-like structures may be connected at one end by the inner lancet 102, and the other end their of takes the form of two separate arc transition structures. Therefore, during a process where the inner lancet 102 folds outwardly, expansion/contraction may occur at the separate arc transition structures, which may lead to an increase of a diameter of the anastomosis clamp in its cylindrical configuration.

To release the above anastomosis clamp, according to the embodiment of the present application, there is also provided with a delivery system for deploying the anastomosis clamp that includes a distal end 2, a middle flexible sheath 3, and a handle 4. The distal end 2 includes a pulling cable 202, a transparent cap 203, and a soft connection cap 204. One end of the soft connection cap 204 is connected to the transparent cap 203, and the other end is connected to an endoscope 5. The pulling cable 202 passes through the transparent cap 203 and is connected to the handle 4 via the middle flexible sheath 3. The anastomosis clamp 1 may be assembled within the transparent cap 203. The anastomosis clamp 1 is pressed against the pulling cable 202, so that the anastomosis clamp 1 to be released, being confined by the transparent cap 203, is in its cylindrical shape.

The distal end 2 of the delivery system for deploying anastomosis clamp has a shape matching with the shape of the anastomosis clamp 1. For example, when the outer rings 201 of the anastomosis clamp 1 together form a discontinuous circular ring, the transparent cap 203 in the distal end 2 also takes the form of a cylindrical tube; on the other end, when the outer rings 201 of the anastomosis clamp 1 together form a discontinuous polygon, the transparent cap 203 in the distal end 2 takes the form of a prismatic tube.

When deploying the anastomosis clamp 1, a pulling force may be applied onto the pulling cable 202 via the handle 4, such that the handle 4 tends to get straightened so as to drive the anastomosis clamp 1 towards the distal end, until the anastomosis clamp 1 slips off the transparent cap 203. As the anastomosis clamp 1 slips off, it is not supported by an inner wall of the transparent cap 203 any more, thus will resume its planar configuration gradually due to its elasticity for the inner lancets 102 to clamp tissues.

What is claimed is:

1. An anastomosis clamp delivery system for deploying an anastomosis clamp (1), comprising a distal end (2), a middle flexible sheath (3), and a handle (4),
   wherein the distal end (2) comprises a pulling cable (202) and a transparent cap (203), and the pulling cable (202) passes through the transparent cap (203) and is connected to the handle (4) via the middle flexible sheath (3); and
   wherein the anastomosis clamp (1) is provided within the transparent cap (203), with the anastomosis clamp (1) being pressed against the pulling cable (202), so that the anastomosis clamp (1) to be released, being confined by the transparent cap (203), is in its cylindrical configuration,
   when deploying the anastomosis clamp (1), a movement of the handle (4) drives the pulling cable (202) to push off the anastomosis clamp (1), such that the anastomosis clamp (1) is released from the delivery system;
   wherein the distal end (2) further comprises a thrust ring (201); wherein
   the thrust ring (201) is placed in the transparent cap (203);
   the pulling cable (202) passes in a loop way and connects the thrust ring (201) and the transparent cap (203);
   the pulling cable (202) that passes the thrust ring (201) and the transparent cap (203) is connected to the handle (4) via the middle flexible sheath (3);
   an axial length of the thrust ring (201) is smaller than that of the transparent cap (203); and
   the dis-continuous ring formed by the outer rings of the anastomosis clamp (1) abuts against the thrust ring (201).

2. The anastomosis clamp delivery system according to claim 1, wherein the pulling cable (202) sequentially passes through the thrust ring (201) and the transparent cap (203), and forms an Ω-like loop structure between the thrust ring (201) and the transparent cap (203).

3. The anastomosis clamp delivery system according to claim 1, wherein the transparent cap (203) has a double-layered structure provided with a first transparent cap holes (2031), a second transparent cap holes (2032), and a connection hole (2034).

4. The anastomosis clamp delivery system according to claim 3, wherein
   one end of the pulling cable (202) threads through two second transparent cap holes (2032) provided at one side of the transparent cap (203),
   the other end of the pulling cable (202) threads through two first transparent cap holes (2031) provided at the respective other side of the transparent cap (203), and
   the two ends of the pulling cable (202) are joined together, and are connected to the handle (4) via the middle flexible sheath (3).

5. The anastomosis clamp delivery system according to claim 1, wherein the anastomosis clamp (1) is sleeved on an inner side of the transparent cap (203), such that the dis-continuous ring formed by the outer rings of the anastomosis clamp (1) abuts against the thrust ring (201), and a tip end of the inner lancets of the anastomosis clamp (1) does not exceed the distal end portion of the transparent cap (203).

6. The anastomosis clamp delivery system according to claim 1, wherein the distal end (2) further comprises a soft connection cap (204); wherein
   one end of the soft connection cap (204) is connected to the transparent cap (203), and the other end is configured to be connectable with an endoscope (5).

7. The anastomosis clamp delivery system according to claim 6, wherein the soft connection cap (204) has a tube configuration made of an elastic material.

8. The anastomosis clamp delivery system according to claim 6, wherein the endoscope (5) may be snap-fitted within the soft connection cap (204).

9. An anastomosis clamp used in cooperation with the anastomosis clamp delivery system according to claim 1, wherein when the anastomosis clamp delivery system is used in cooperation with the anastomosis clamp, the anastomosis clamp (1) is provided within the transparent cap (203), with the anastomosis clamp (1) being pressed against the pulling cable (202), so that the anastomosis clamp (1) to be released, being confined by the transparent cap (203), is in its cylindrical configuration.

10. The anastomosis clamp according to claim 9, comprising:
    a plurality of outer rings, round corners, and inner lancets that are sequentially connected, with the whole connection structure being central symmetric;
    wherein the plurality of outer rings are spaced apart and are discontinuous, with adjacent discontinuous outer rings being connected via the round corners;
    wherein each round corner is provided with an inner lancet that is pointedly configured;
    wherein in a direction from the outer ring towards a center point of the symmetric connection structure, two round corners configured to curve in opposite directions are connected to form an S-like shape that connects the inner lancet to the outer ring; and
    wherein in the obtained connection structure, arc transitions are formed between the outer rings and the round corners.

11. The anastomosis clamp according to claim 1, comprising:
    a plurality of outer ring segments (101), round corners (103), and inner lancets (102) that are sequentially connected;
    wherein an end of each of the plurality of the outer ring segments (101) is successively connected to two round corners (103) that are curved in opposite directions as so form an S-like shape between each of the outer ring segment (101) and an inner lancet (102);
    wherein the plurality of outer ring segments (101) forms discontinuous sections of a ring-shaped structure;
    wherein each inner lancet (102) is arranged between two adjacent outer ring segments (101) with two outer end of the inner lancet (102) being respectively connected to two said S-like structures, so that these two adjacent outer ring segments (101) are axially-symmetric arranged with respect to each inner lancet (102), wherein the inner end of each inner lancet (102) has a pointed configuration.

12. The anastomosis clamp according to claim 11, wherein the plurality of inner lancets (102) are central-symmetrically arranged on the ring shaped structure formed by the outer rings (101).

13. The anastomosis clamp according to claim 11, wherein the plurality of outer rings (101) are separately arranged by the round corners (103); and
    wherein the plurality of outer rings (101) together form a dis-continuous circular ring structure or a dis-continuous polygon structure.

14. The anastomosis clamp according to claim 11, wherein the inner lancet (102) comprises a plurality of sharp corners that are axial-symmetrically arranged at both sides with respect to the tip of the inner lancet (102), so as to aid a piercing and clamping of tissues that need to be clamped.

15. The anastomosis clamp according to claim 11, Wherein the plurality of outer rings (101), round corners (103), and inner lancets (102) together form an integral structure made of a hyperelastic material.

* * * * *